(12) United States Patent
Park et al.

(10) Patent No.: US 11,684,808 B2
(45) Date of Patent: Jun. 27, 2023

(54) HIGH INTENSITY FOCUSED ULTRASONIC SURGICAL DEVICE WITH ECCENTRIC DRIVING CAM

(71) Applicant: Jong Chul Park, Suwon-si (KR)

(72) Inventors: Jong Chul Park, Suwon-si (KR); Hee Sook Lee, Suwon-si (KR)

(73) Assignee: Jong Chul Park, Suwon-si (KR)

( * ) Notice: Subject to any disclaimer, the term of this patent is extended or adjusted under 35 U.S.C. 154(b) by 871 days.

(21) Appl. No.: 16/480,179

(22) PCT Filed: Nov. 17, 2017

(86) PCT No.: PCT/KR2017/013071
§ 371 (c)(1),
(2) Date: Jul. 23, 2019

(87) PCT Pub. No.: WO2018/143544
PCT Pub. Date: Aug. 9, 2018

(65) Prior Publication Data
US 2019/0366129 A1    Dec. 5, 2019

(30) Foreign Application Priority Data

Jan. 31, 2017 (KR) .................. 10-2017-0013457
Nov. 2, 2017 (KR) .................. 10-2017-0145131

(51) Int. Cl.
*A61N 7/02* (2006.01)
*A61N 7/00* (2006.01)

(52) U.S. Cl.
CPC .............. *A61N 7/02* (2013.01); *A61N 7/00* (2013.01); *A61N 2007/0091* (2013.01)

(58) Field of Classification Search
CPC .... A61N 7/02; A61N 7/00; A61N 2007/0091; A61N 2007/0082
See application file for complete search history.

(56) References Cited

U.S. PATENT DOCUMENTS 4,442,842 A *  4/1984  Baba .................. A61B 1/2736
                                              73/620
5,443,068 A     8/1995  Cline et al.
                        (Continued)

FOREIGN PATENT DOCUMENTS

EP      2422708 A1    2/2012
JP   2004526517 A    9/2004
                (Continued)

OTHER PUBLICATIONS

European Patent Office, Munich, Germany, dated Jul. 1, 2020, Application No./Patent No. PCT/KR2017013071, Applicant/Proprietor: Park, Jong Chul, Communication, Extended European Search Report.

(Continued)

*Primary Examiner* — Serkan Akar
*Assistant Examiner* — Neshat Baset
(74) *Attorney, Agent, or Firm* — Flener IP & Business Law; Zareefa B. Flener

(57) ABSTRACT

The present invention relates to an ultrasonic surgical device in which a cartridge comprises: a cartridge housing having an empty inner space filled with a medium; an ultrasonic therapy part which is movably provided inside the cartridge housing and includes a transducer for generating focused ultrasonic waves; a window through which the ultrasonic waves generated from the transducer pass; and a driving part which moves the ultrasonic therapy part inside the cartridge housing, wherein, as the transducer moves in one direction, the distance between the window and the transducer repeatedly increases and decreases.

15 Claims, 9 Drawing Sheets

(56) References Cited

U.S. PATENT DOCUMENTS

| | | | | |
|---|---|---|---|---|
| 2007/0062290 A1* | 3/2007 | Roh | ................... | G01N 29/221 |
| | | | | 73/634 |
| 2014/0276055 A1* | 9/2014 | Barthe | ............... | A61B 8/4466 |
| | | | | 600/439 |
| 2017/0303895 A1* | 10/2017 | Park | ..................... | A61B 8/44 |

FOREIGN PATENT DOCUMENTS

| | | | | | |
|---|---|---|---|---|---|
| KR | 20120040909 A | | 4/2012 | | |
| KR | 101191347 B1 | | 10/2012 | | |
| KR | 20150115432 A | * | 4/2014 | ............ | A61H 23/02 |
| KR | 20140067482 A | | 6/2014 | | |
| KR | 20150115432 A | | 10/2015 | | |
| KR | 20160063119 A | | 6/2016 | | |
| KR | 20160103760 A | | 9/2016 | | |
| KR | 101756618 | | 1/2017 | | |
| WO | 2014/081062 A1 | | 5/2014 | | |

OTHER PUBLICATIONS

International Search Report, International Application No. PCT/KR2017/013071.
Republic of Korea Office action for KR1020170145131 (untranslated).

\* cited by examiner

HIGH INTENSITY FOCUSED ULTRASONIC SURGICAL DEVICE WITH ECCENTRIC DRIVING CAM

TECHNICAL FIELD

The present invention relates to an ultrasonic surgical device.

BACKGROUND ART

A variety of operations for improving skin conditions, including, for example, a skin tightening operation or a face lifting operation, or operations for reducing subcutaneous fat layer, are being developed nowadays. Such operations are largely divided into an invasive type and a non-invasive type. Ultrasonic medical devices performing operations for tissue regeneration or removal by forming thermal focal points at tissue, such as a predetermined portion of muscle or a subcutaneous fat layer, by irradiating intensity focused ultrasound (IFU) into the interior of the skin tissue, are also being proposed.

Technical Problems to be Solved

An embodiment of the present invention provides an ultrasonic surgical device having improved efficiency or stability of an operation using ultrasonic waves.

Technical Solutions

In accordance with an aspect of the present invention, the above and other objects can be accomplished by providing an ultrasonic surgical device including a cartridge for irradiating ultrasonic waves, the cartridge comprising: a cartridge housing having an empty inner space filled with a medium; an ultrasonic therapy part which is movably provided inside the cartridge housing and includes a transducer for generating focused ultrasonic waves; a window through which the ultrasonic waves generated from the transducer pass; and a driving part which moves the ultrasonic therapy part inside the cartridge housing, wherein, as the transducer moves in one direction, the distance between the window and the transducer repeatedly increases and decreases.

Here, the driving part may be shaped of a cylinder and may include an eccentric driving cam passing a spot spaced apart from the center axis of the cylinder; the ultrasonic therapy part may include a connecting rod having one side coupled to an outer surface of the eccentric driving cam and a connector coupled to the other side of the connecting rod; and the transducer may move according to clockwise rotation of the eccentric driving cam.

In addition, the one direction may range from one end to the other end of the cartridge housing; if the eccentric driving cam rotates in a clockwise direction, the transducer may move in the one direction; if the eccentric driving cam rotates in a counterclockwise, the transducer may move from the other end to the one end of the cartridge housing, and the distance between the window and the transducer may repeatedly increase and decrease.

In addition, the ultrasonic surgical device may further include a guide arm functioning to guide the ultrasonic therapy part to move forward, to move backward, to move upward and to move downward, as the orientation of a bottom surface of the transducer is constantly maintained on the basis of the window, wherein the connecting rod is rotatably coupled to the connector, and the connector ascends and descends while being supported on a surface contacting the guide arm.

In addition, the ultrasonic surgical device may further include a guide arm functioning to guide the ultrasonic therapy part to move forward, to move backward, to move upward and to move downward, as the orientation of a bottom surface of the transducer is constantly maintained on the basis of the window, wherein the ultrasonic surgical device further includes a guide pin protruding upwardly relative to the transducer; the guide arm further includes a guide pin hole for accommodating the guide pin; and as the guide pin is supported on an inner wall of the guide pin hole, the transducer ascends and descends to make the orientation of the bottom surface of the transducer constantly maintained on the basis of the window.

In addition, the ultrasonic surgical device may further include a guide arm functioning to guide the ultrasonic therapy part to move forward, to move backward, to move upward and to move downward, as the orientation of a bottom surface of the transducer is constantly maintained on the basis of the window, wherein the connecting rod is rotatably coupled to the connector; the connector ascends and descends as it is supported on a surface contacting the guide arm; the ultrasonic surgical device further includes a guide pin protruding upwardly relative to the transducer; and the guide arm further includes a guide pin hole for accommodating the guide pin; and as the guide pin is supported on an inner wall of the guide pin hole, the transducer ascends and descends to make the orientation of the bottom surface of the transducer constantly maintained on the basis of the window.

In addition, the ultrasonic surgical device may further include a guide rail disposed to be parallel with a rotation axis of the driving cam inside the cartridge housing, wherein the guide arm moves forward and backward while being supported on the guide rail.

In addition, the eccentric driving cam may include a shaft made of a metallic material, and a body part shaped of a cylinder and made of a synthetic resin, wherein the rotation axis of the eccentric driving cam is a center axis of the shaft.

In addition, one side of the connecting rod may be shaped of a ring covering the eccentric driving cam.

In addition, the driving part may include a driving cam rotatably coupled inside the cartridge housing; and a first recess provided along the outer surface of the driving cam, and the ultrasonic therapy part may include a guide part fixed to the transducer; and an insertion pin having one side movably inserted into the first recess along the first recess and the other side fixed to the transducer or the guide part, wherein the trajectory of a first contact point having the shortest distance from the rotation axis of the driving cam, among contact points between the insertion pin and the first recess, is established according to the rotation of the driving cam, such that the distance between the rotation axis of the driving cam and the first contact point increases or decreases.

Here, the ultrasonic surgical device may further include an elastic member that generates an elastic force allowing the insertion pin to be pressed toward the first recess.

In addition, the ultrasonic surgical device may further include a guide rail disposed to be parallel with the rotation axis of the driving cam inside the cartridge housing, wherein the guide part further includes a guide groove into which the guide rail is inserted, and a distance between a top surface of the guide rail and the guide groove increases or decreases.

In addition, the driving part may include a driving cam rotatably coupled inside the cartridge housing; and a first protrusion provided along the outer surface of the driving cam, and the ultrasonic therapy part may include a guide part fixed to the transducer, wherein one side of the first protrusion is brought into contact with the transducer or the guide part; and the trajectory of a second contact point having the shortest distance from the rotation axis of the driving cam, among contact points between the first protrusion and the transducer or the guide part, is established according to the rotation of the driving cam, such that the distance between the rotation axis of the driving cam and the second contact point increases or decreases in a spiral form.

In addition, the ultrasonic surgical device may further include an elastic member that generates an elastic force allowing the transducer or the guide part to be pressed toward the first recess.

In addition, the ultrasonic surgical device may further include a position sensor for detecting the position of the transducer.

Advantageous Effects

As described above, according to an embodiment of the present invention, the operating time can be shortened, and operator's fatigue can be reduced. According to an embodiment of the present invention, the operator's fatigue can be reduced while reducing the risk generated due to overlapping of thermal focal points.

BEST MODE FOR CARRYING OUT THE INVENTION

Figure 1:
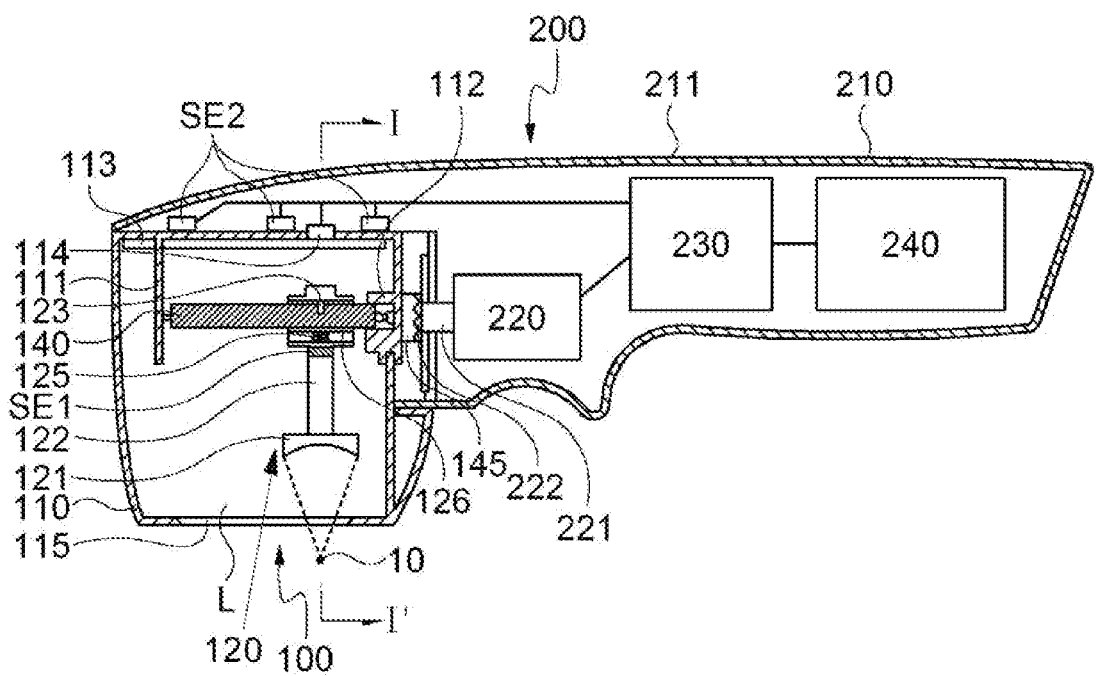
FIG. 1 is a schematic diagram illustrating an ultrasonic surgical device according to an embodiment of the present invention.
Figure 2:
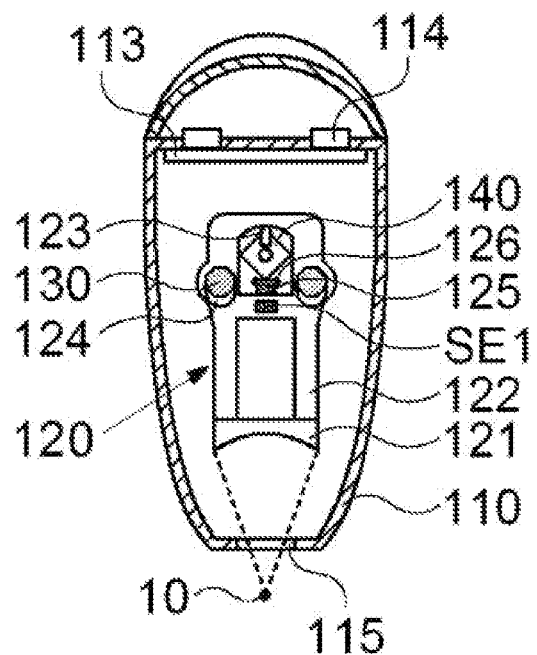
FIG. 2 is a schematic diagram illustrating a cartridge of the ultrasonic surgical device according to an embodiment of the present invention.

Hereinafter, configurations and functional effects of the present invention will be described in more detail with reference to the accompanying drawings.

Embodiment 1

Referring to the drawings, the ultrasonic surgical device 1000 according to an embodiment of the present invention may be a medical device performing various operations using intensity focused ultrasound (IFU). In this case, a high intensity focused ultrasound (to be referred to as 'HFU' hereinafter) having a relatively high intensity of focused ultrasound waves can be used. In another embodiment, when necessary, a low intensity focused ultrasound (to be referred to as 'LIFU' hereinafter) having a relatively low intensity of focused ultrasound waves can be used.

The ultrasonic surgical device 1000 according to an embodiment of the present invention may include a cartridge 100 and a handpiece 200. In an embodiment, the cartridge 100 may be attached to/detached from the handpiece 200. Accordingly, when a breakdown occurs to the cartridge 100 or when the cartridge 100 reaches the end of its life span, the cartridge 100 may be replaced with a new one to perform the operation.

In addition, different cartridges 100 implemented for performing operations having different purposes may be replaceably attached to the handpiece 200, thereby performing various types of operations using one single handpiece 200.

Even if operation purposes of different operations are the same, the cartridge 100 designed by varying specific features, including diameters of thermal focal points 10, distances from the skin surface to the thermal focal points 10, distances between the thermal focal points 10, etc., may be replaceably attached to the handpiece 200, thereby performing operations using the thermal focal points 10 having characteristics optimized to the operations.

In an embodiment, although not shown, a cartridge may be integrally implemented with a handpiece, rather than being attached to/detached from the handpiece. Even in this case, however, a space between a transducer and a window is preferably filled with a medium.

In an embodiment, the operator may perform an operation by irradiating intensity focused ultrasound (IFU) into an operation target portion in a state in which a position of the cartridge 100 is adjusted so as to make the cartridge 100 come into contact with the operation target portion by holding a portion of the handpiece 200 by hand. To this end, a handle part 211 may be provided in the handpiece 200. In an embodiment, the handle part 211 may be implemented by ergonomically forming a portion to be grasped by the operator in a handpiece housing 210 constituting the outer case of the handpiece 200.

Although not shown, a display device providing the operator with operation related information, an input device receiving operator's instruction, or the like, may also be provided.

In an embodiment, a power supply unit 240 may be provided within the handpiece 200. According to this embodiment, the operation can be administered by freely moving the handpiece 200, like in a case of using an electric shaving device, thereby enhancing convenience in performing the operation.

Although not shown, a separate cable may be connected to the handpiece 200 to exchange power or control signals between the handpiece 200 and other devices.

In an embodiment, the cartridge 100 may include a cartridge housing 110, an ultrasonic therapy part 120, a window 115 and a driving part 140.

In an embodiment, the cartridge housing 110 may be a kind of a case defining the outer walls of the cartridge 100. Various kinds of parts may be provided in an inner space of the cartridge housing 110, and an empty space excluding portions corresponding to the parts in the inner space may be filled with a medium L. The medium L may serve as a kind of a transfer medium for smoothly transferring IFU waves emitted from the transducer 121 to the exterior of the cartridge housing 110. In addition, the medium L may perform a function of cooling heat generated from the transducer 121 in the course of producing the IFU waves.

In an embodiment, the ultrasonic therapy part 120 may include the transducer 121 provided within the cartridge housing 110 and generating the IFU waves. Moreover, the ultrasonic therapy part 120 may include a guide part 122 coupled to the transducer 121. In addition, the ultrasonic therapy part 120 may further include an insertion pin 123, a guide groove 124, an elastic member 125, and a contact plate 126.

In an embodiment, the IFU waves generated by the transducer 121 are transferred to the exterior of the cartridge 100 via the window 115. Therefore, the window 115 is preferably formed using a material to a thickness so as to be affected by the IFU waves as little as possible. That is to say, it is preferable to make the window 115 undergo little changes in the intensity, characteristic, direction, etc. of the IFU waves.

In an embodiment, the driving part 140 may perform a function of transferring the ultrasonic therapy part 120. Here, the ultrasonic therapy part 120 may move forward or backward inside the cartridge housing 110. Referring to FIG. 1, one part of the cartridge housing 110 close to a motor 220 may be one end of the cartridge housing 110 and the opposite part may be the other end of the cartridge housing 110. In this case, moving in a direction from the one end to the other end of the cartridge housing 110 may correspond to forward movement, and moving in the opposite direction may correspond to backward movement.

In an embodiment, while the ultrasonic therapy part 120 is moving forward, heights of the ultrasonic therapy part 120 may vary. For example, supposing that the IFU waves are downwardly emitted from the ultrasonic therapy part 120, the relative height of the ultrasonic therapy part 120 may increase or decrease inside the cartridge housing 110. In addition, the ultrasonic therapy part 120 may move while passing at least one or more sections, including a first section (S1 of FIG. 10) in which the height of the ultrasonic therapy part 120 increases as the ultrasonic therapy part 120 moves forward, and a second section (S2 of FIG. 10) in which the height of the ultrasonic therapy part 120 decreases as the ultrasonic therapy part 120 moves forward.

Although not shown, as the ultrasonic therapy part 120 moves backward, the height of the ultrasonic therapy part 120 may also vary. In addition, sections in which the height of the ultrasonic therapy part 120 increases according to backward movement of the ultrasonic therapy part 120, and sections in which the height of the ultrasonic therapy part 120 decreases according to backward movement of the ultrasonic therapy part 120, may also be implemented.

In an embodiment, if the height of the ultrasonic therapy part 120 increases, the distance between the transducer 121 and the window 115 may increase, and if the height of the ultrasonic therapy part 120 decreases, the distance between the transducer 121 and the window 115 may decrease.

In an embodiment, the driving part 140 may include a driving cam 141. The driving cam 141 may be installed to rotate about a predetermined rotation axis inside the cartridge housing 110. In an embodiment, means for fixing the driving cam 141 may be provided inside the cartridge housing 110. As illustrated in FIG. 1, a first frame 111 is provided at the other side of the cartridge 100 to allow the other end of the driving cam 141 to be rotatably coupled thereto, and a second frame 112 is provided at one side of the cartridge 100 to allow the one end of the driving cam 141 to be rotatably coupled thereto.

Meanwhile, a second rotating part 145 having at least a portion exposed to the exterior of the cartridge housing 110 may be physically connected to the one end of the driving cam 141, thereby rotating the driving cam 141 according to rotation of the second rotating part 145. Here, in order to prevent the medium L from being effused through a gap between a portion of the one end of the driving cam 141 passing the cartridge housing 110 or a portion of the second rotating part 145 passing the cartridge housing 110, and the cartridge housing 110, a sealing member (not shown) for securing air tightness may be provided.

Figure 3:
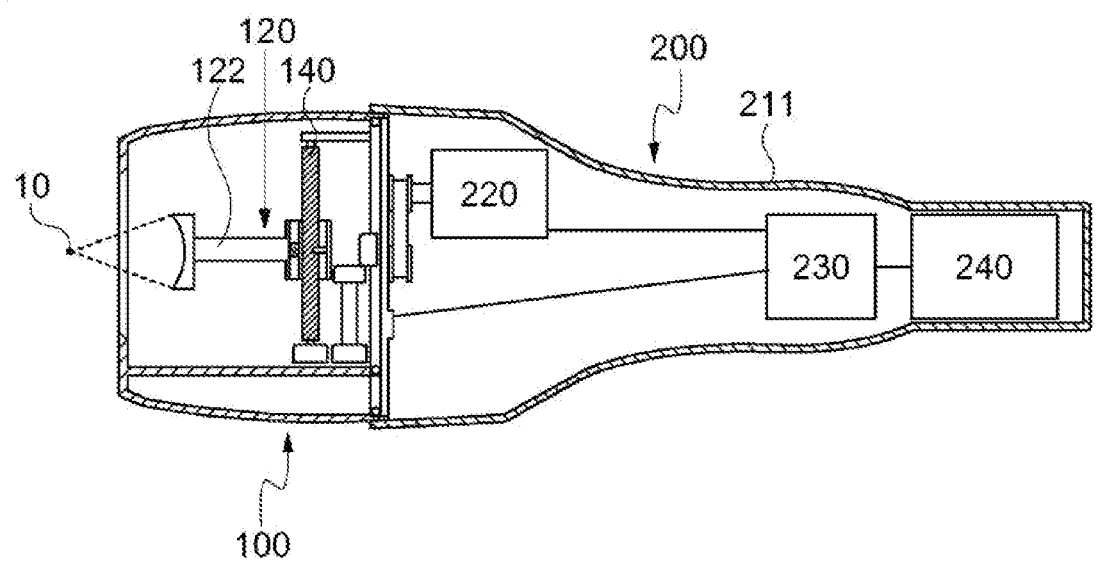
FIG. 3 is a schematic diagram illustrating a modified example of the ultrasonic surgical device according to an embodiment of the present invention.

Successively, referring to FIG. 1, the motor 220 may be provided in the handpiece 200, and a first rotating part 222 connected to a motor drive shaft 221 may impart a rotation force (torque) to the second rotating part 145. In an embodiment, as illustrated in FIG. 1, the rotation axis of the driving cam 141 may be parallel with the motor drive shaft 221. In another embodiment, as illustrated in FIG. 3, the rotation axis of the driving cam 141 may be perpendicular to the drive shaft of the motor 220. The structure illustrated in FIG. 1 may be called a gun type, and the structure illustrated in FIG. 3 may be called a bar type.

In an embodiment, a circuit board for connecting a power source or signal lines may be provided in a third frame 113 illustrated in FIG. 1. A terminal part 114 is provided in the circuit board so as to be exposed to the exterior of the cartridge housing 110, thereby electrically connecting the handpiece 200 and the terminal part 114. In an embodiment, the terminal part 114 may be connected to a control part 230 of the handpiece 200.

In an embodiment, the ultrasonic therapy part 120 may be movably coupled to the driving cam 141. In addition, as the driving cam 141 rotates, the ultrasonic therapy part 120 may ascend while moving forward, may descend while moving forward, may ascend while moving backward and may descend while moving backward.

Figure 4:
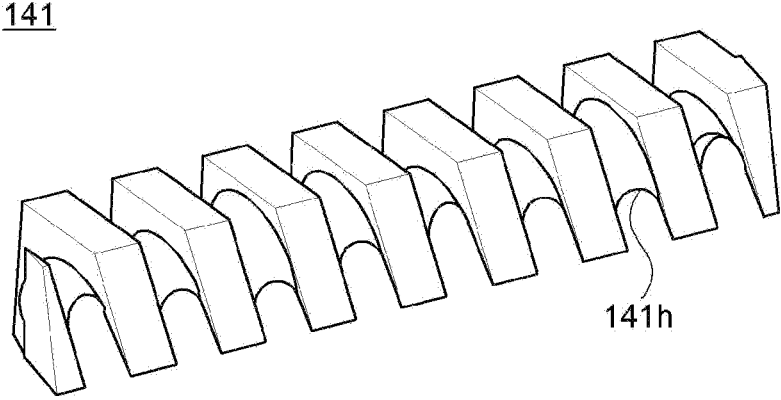
FIG. 4 is a schematic diagram illustrating a major part of the ultrasonic surgical device according to an embodiment of the present invention.
Figure 5:
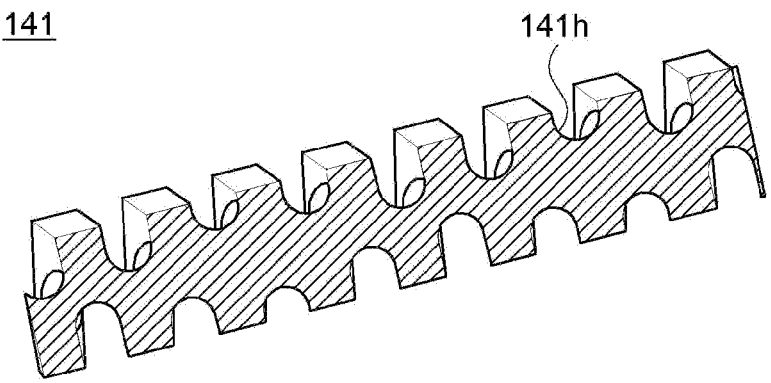
FIG. 5 is a schematic diagram illustrating a cross section of the major part shown in FIG. 4.
Figure 6:
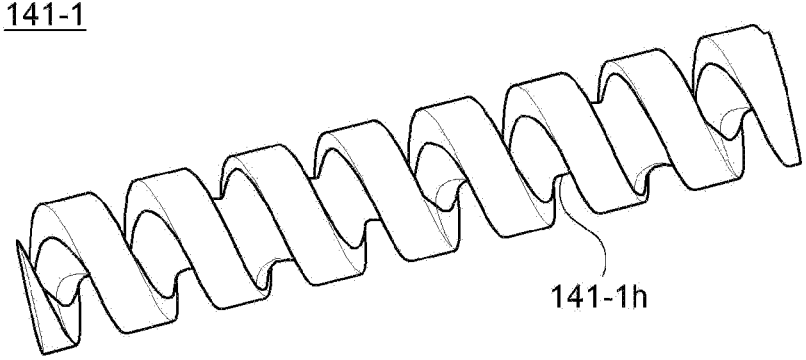
FIG. 6 is a schematic diagram illustrating a modified example of the major part shown in FIG. 4.

In an embodiment, the driving cam 141 may be pillar shaped. Here, the driving cam 141 may be shaped of a polygonal pillar, including, for example, a square pillar. In addition, the driving cam 141 may be shaped of a cylinder. FIG. 4 illustrates an embodiment of the driving cam 141 shaped of a square pillar, and FIG. 6 illustrates an embodiment of a driving cam 141-1 shaped of a cylinder.

Figure 7:
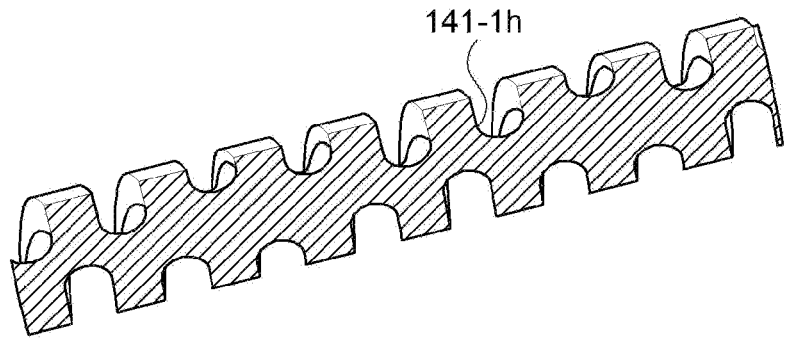
FIG. 7 is a schematic diagram illustrating a cross section of the modified major part shown in FIG. 6.

In an embodiment, a first recess 141h (or 141-h in FIG. 6 and FIG. 7) may be provided on an outer surface of the driving cam 141. The first recess 141h may be continuously connected from one side to the other side of the driving cam 141 while rotating about the rotation axis of the driving cam 141. Accordingly, the first recess 141h may have a substantially spiral trajectory.

Figure 8:
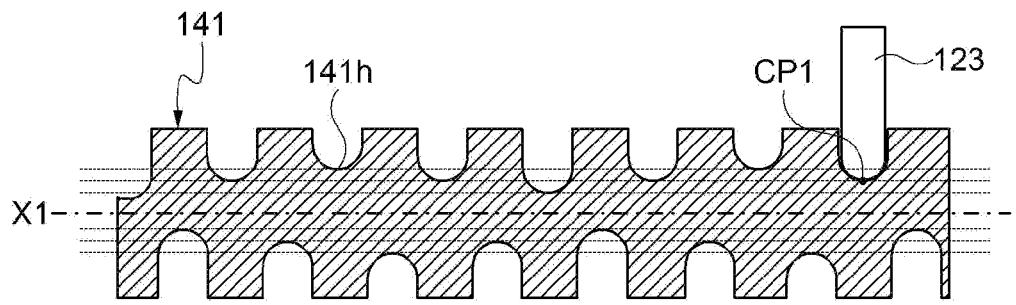
FIG. 8 is a diagram for explaining an operating principle of the ultrasonic surgical device according to an embodiment of the present invention.

In an embodiment, the insertion pin 123 may be provided in the guide part 122, and the insertion pin 123 may be inserted into the first recess 141h. FIG. 8 illustrates an example embodiment in which the insertion pin 123 is inserted into the first recess 141h and comes into contact therewith. Among contact points between the insertion pin 123 and the first recess 141h, the contact point closest to the rotation axis of the driving cam 141 may be defined as a first contact point CP1. Although FIG. 8 shows that the lowest point of the insertion pin 123 contacts the lowest point of the first recess 141h, a point of the insertion pin 123, which is not the lowest point, or a point of the first recess 141h, which is not the lowest point, may become the first contact point according to shapes of the insertion pin 123 and the first recess 141h.

Figure 9:
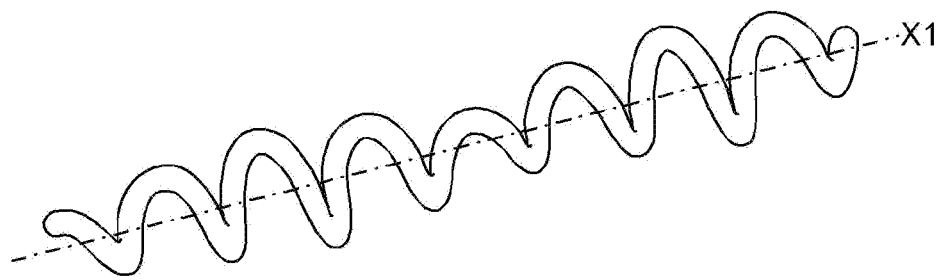
FIG. 9 is a diagram for explaining an operating principle of the ultrasonic surgical device according to an embodiment of the present invention.

According to an embodiment of the present invention, locations of the points that become the first contact point CP1 may be connected, as represented by the example illustrated in FIG. 9. That is to say, the distance from the first contact point CP1 to the rotation axis of the driving cam 141 may increase or decrease. In addition, the first contact point CP1 may form a spiral trajectory from one side to the other side of the driving cam rotation axis X1 as the driving cam 141 moves about the driving cam rotation axis X1. In this case, the distance between the driving cam rotation axis X1 and the first contact point CP1 may also increase or decrease.

In an embodiment, if the driving cam 141 is rotated, the ultrasonic therapy part 120, including the insertion pin 123, may ascend while moving forward, or may descend while moving forward.

Figure 10:
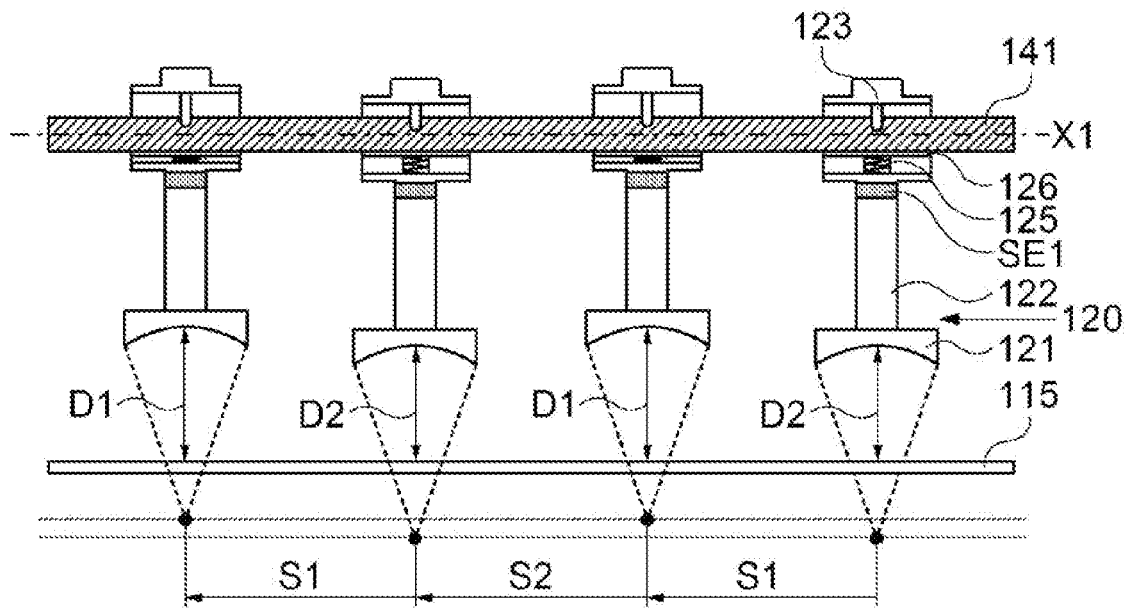
FIG. 10 is a diagram for explaining an operating principle of the ultrasonic surgical device according to an embodiment of the present invention.
Figure 11:
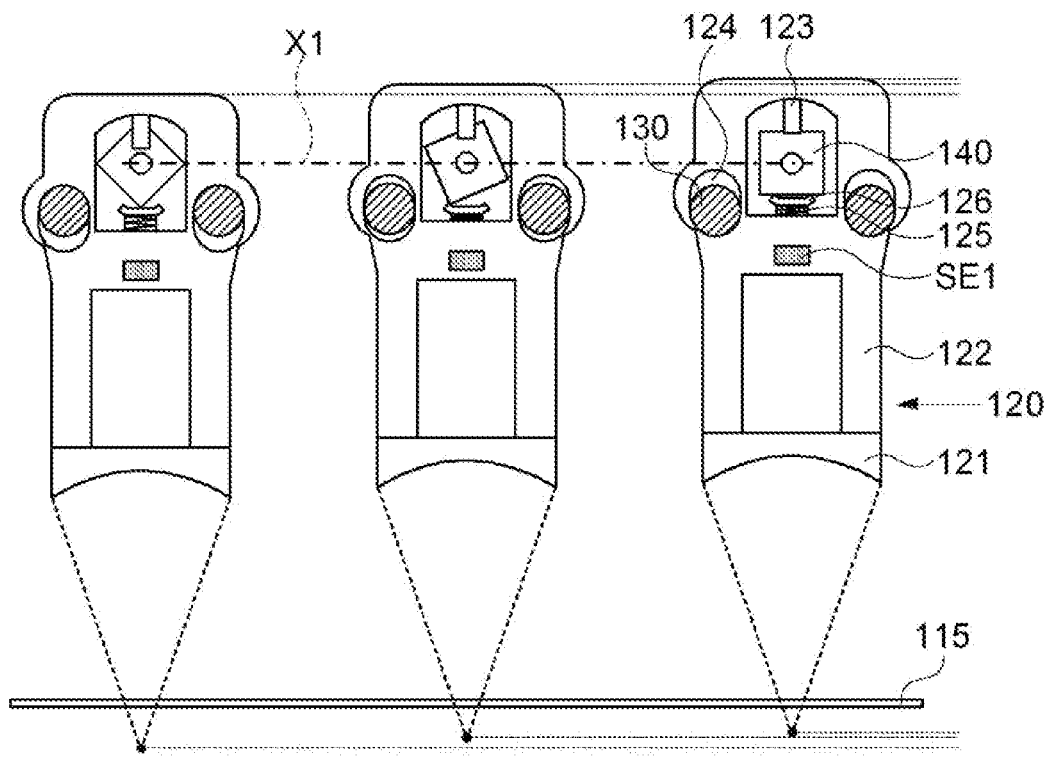
FIG. 11 is a diagram for explaining an operating principle of the ultrasonic surgical device according to an embodiment of the present invention.

In an embodiment, as illustrated in FIG. 10, according to the rotation of the driving cam 141, the ultrasonic therapy part 120 positioned at one side of the driving cam 141 may ascend while moving forward, which is shown as the first section S1. In addition, according to the rotation of the driving cam 141, the ultrasonic therapy part 120 may descend while moving forward, which is shown as the second section S2.

In an embodiment, the extent of the driving cam 141 ascending per revolution while moving forward, or the extent of the driving cam 141 descending per revolution while moving backward, may be determined in consideration of at least one value of the diameter of thermal focal points 10 generated by the ultrasonic therapy part 120, the distance between the thermal focal points 10 required for achieving purposes of operations and securing safety, and the thickness of an operation target range (i.e., the thickness of a tissue where the thermal focal points 10 need to be formed).

Figure 12:
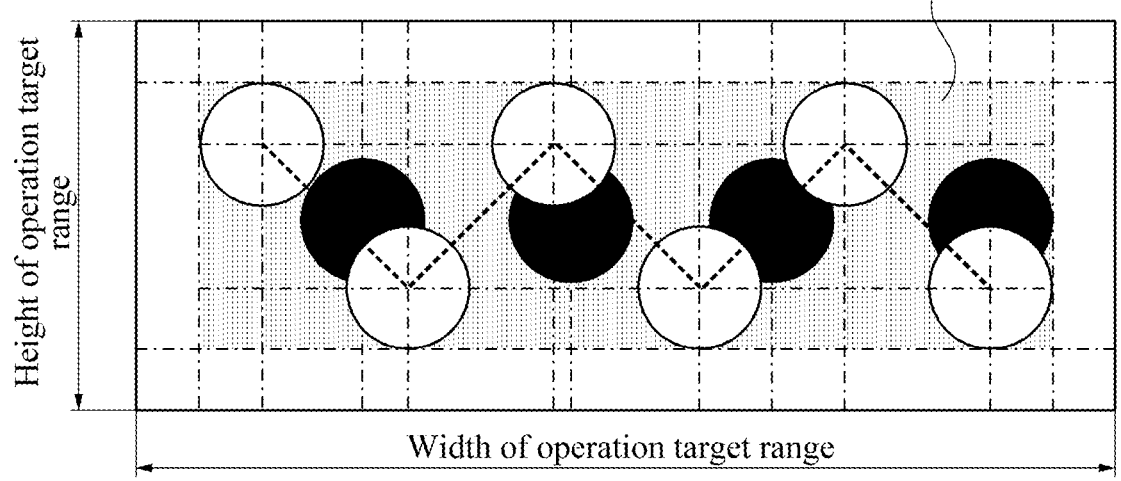
FIG. 12 is a diagram for explaining an operating principle of the ultrasonic surgical device according to an embodiment of the present invention.

Referring to FIG. 12, in a case where thermal focal points 10 need to be positioned as densely as possible, the operation may be administered using the cartridge 100 including the driving cam 141 designed such that the linear distance of the driving cam 141 ascending while moving forward is a minimum allowable distance between the thermal focal points 10, and the first section and the second section are alternately repeated. Here, a process of the ultrasonic transducer 121 forming the thermal focal points 10 is called a shot, and the operation may be administered in such a manner that a first shot is delivered, a second shot is delivered after passing the first section, a third shot is delivered after moving the second section, a fourth shot is delivered after passing the first section, and then a fifth shot is delivered after passing the second section. In this way, the number of shots delivered within unit distance can be maximized, thereby forming the thermal focal points 10 as densely as possible.

As illustrated in FIG. 12, in a case where thermal focal points 10 need to be positioned as densely as possible while securing safety of the operation to be administered on the operation target range having the same height and width, more shots can be delivered using the ultrasonic surgical device 1000 according to an embodiment of the present invention than the conventional surgical device in which shots are delivered along a single line at a single height. Therefore, it will be understood that the operation efficiency and operating effect can be improved while securing safety of the operation. Although not shown, two or more shots may be delivered while passing the first section and the second section, respectively.

In an embodiment, if the driving cam 141 is rotated, the ultrasonic therapy part 120 including the insertion pin 123 may ascend while moving backward or may descend while moving backward. Since specific details are similar to those stated above, a redundant explanation will be omitted.

Referring to FIG. 10, in an embodiment, the transducer 121 is coupled to a lower portion of the guide part 122, and an upper portion of the guide part 122 may be positioned above the driving cam 141. In addition, the insertion pin 123 provided on the guide part 122 may face the first recess 141h of the driving cam 141. With this configuration, the insertion pin 123 may be pressed toward the first recess 141h due to weights of the transducer 121 and the guide part 122. Accordingly, as the depth of the first recess 141h increases, the insertion pin 123 may be inserted deeply toward the first recess 141h and the ultrasonic therapy part 120 may descend. However, according to the shapes of the insertion pin 123 and the first recess 141h or the intensity of friction, the insertion pin 123 cannot be sufficiently pressed toward the first recess 141h due to only the weight of the ultrasonic therapy part 120. In addition, in a case where the operation target surface is not parallel with the ground surface but is inclined with respect to the ground surface, the overall structure of the cartridge 100, including the window 115, may be inclined. Accordingly, the irradiation direction of the IFU waves may not be parallel with a gravity direction but may be inclined with respect to the gravity direction. In this case, the insertion pin 123 may not be sufficiently pressed toward the first recess 141h by only the weight of the ultrasonic therapy part 120.

As described above, if the insertion pin 123 is not sufficiently pressed toward the first recess 141h, positions of the first contact point CP1 may vary within the first recess 141h, the ascending or descending operation of then ultrasonic therapy part 120 based on the designed dimensions may not be smoothly performed. To solve this problem, the ultrasonic surgical device 1000 according to an embodiment of the present invention may include an elastic member 125. The elastic member 125 may perform a function of imparting an elastic force for pressing the insertion pin 123 toward the first recess 141*h*. Here, as illustrated in FIGS. 1 and 10, a top end of the elastic member 125 may be brought into contact with a bottom end of the driving cam 141, and a bottom end of the elastic member 125 may be coupled to the guide part 122. Accordingly, the guide part 122 may be pressed toward a lower portion of the driving cam 14. As a result, the insertion pin 123 provided in the guide part 122 may be pressed toward the first recess 141*h*. Meanwhile, as the driving cam 141 according to the embodiment of the present invention is rotated, the elastic member 125 may be separated or deformed due to the rotation of the driving cam 141. To avoid this, the contact plate 126 may be provided at the top end of the elastic member 125 so as to come into contact with the driving cam 141.

Although not shown, if the insertion pin 123 is positioned at the lower portion of the driving cam 141, the bottom end of the elastic member 125 may be brought into contact with the top end of the driving cam 141, and the top end of the elastic member 125 may be coupled to the guide part 122, thereby offering an elastic force to the guide part 122 to upwardly push the guide part 122.

In an embodiment, a guide rail 130 may be provided inside the cartridge housing 110. The guide rail 130 may allow the guide part 122 to stably move forward or backward while being in contact with the guide part 122.

In an embodiment, the guide rail 130 may be fixed inside the cartridge housing 110 so as to be parallel with the rotation axis of the driving cam 141. For example, one end of the guide rail 130 may be coupled to the first frame 111 and the other end thereof may be coupled to the second frame 112. Meanwhile, a guide groove 124, into which the guide rail 130 is inserted, may be provided in the guide part 122. Here, the ultrasonic therapy part 120 of the ultrasonic surgical device 1000 according to an embodiment of the present invention may ascend or descend while moving forward or backward. In addition, the guide rail 130 may be shaped of a straight line parallel with the driving cam 141. In this case, if the guide rail 130 and the guide groove 124 are engaged with each other while a top surface of the guide rail 130 and a bottom surface of the guide rail 130 are concurrently brought into contact with the guide groove 124, it may be difficult to achieve the ascending or descending operation of the guide part 122. Therefore, the ultrasonic surgical device 1000 according to an embodiment of the present invention is preferably implemented such that the distance between the top surface of the guide rail 130 and the guide groove 124 increases or decreases, which is illustrated in FIG. 8 by way of example. Although not shown, a bearing may be provided between the top surface of the guide rail 130 and the guide groove 124, a spring for pressing the bearing toward the guide rail 130 may be provided, and the insertion pin 123 may be pressed toward the first recess 141*h* by means of the spring.

Although not shown, in an embodiment, a first protrusion outwardly protruding from the surface of the driving cam 141 may be provided, instead of the first recess 141*h* concaved from the surface of the driving cam 141 in an axial direction of the driving cam 141. In this case, the first protrusion may be brought to the guide part 122 or the transducer 121. Among contact points between the first protrusion and the guide part 122 or the transducer 121, the contact point closest to the rotation axis of the driving cam 141 may be defined as a second contact point CP2. The second contact point CP2 may be implemented to have the same features as the first contact point CP1. In addition, in this embodiment, the elastic member 125 may also be provided, and the elastic member 125 may be pressed toward the first protrusion by the transducer 121 or the guide part 122.

According to an embodiment of the present invention, the position of the ultrasonic therapy part 120 can be detected. To this end, various kinds of sensors, including an IR sensor, a hall sensor, or a photo sensor, may be employed. For example, as illustrated, the guide part 122 may include a first sensor SE1. Here, the first sensor SE1 may be implemented by the IR sensor. If the first sensor SE1 includes an IR emitting part, an IR receiving part (not shown) may be positioned opposite to the first sensor SE1 (e.g., a spot positioned on the first frame 111).

Meanwhile, the first sensor SE1 may include an IR emitting part and an IR receiving part. In this case, a reflecting part (not shown) made of a material capable of reflecting IR rays may be positioned opposite to the first sensor SE1. In the structure illustrated in FIG. 1, the reflecting part may be provided in the first frame 111.

In an embodiment, a second sensor SE2, which is implemented by at least one or more hall sensors or photo sensor, may be provided at an upper portion of the cartridge 100. Here, the second sensor SE2 may be provided in the handpiece 200. In this case, the cartridge housing 110, etc. needs to be implemented using a material that does not interrupt the second sensor SE2 in detecting the position of the ultrasonic therapy part 120. For example, if the second sensor SE2 is implemented by a photo sensor, components positioned between a reference region for detecting the position of the ultrasonic therapy part 120, and the second sensor SE2, including the cartridge housing 110, are preferably made of a material having high transmissivity. Accordingly, the second sensor SE2 provided in the handpiece 200 may be shared by multiple cartridges 100. In another embodiment, the second sensor SE2 may be provided within the cartridge housing 110. In this case, however, the manufacturing cost of the cartridge 100 may undesirably rise.

In an embodiment, a sensor provided inside the cartridge housing 110 may be electrically connected to the control part 230 through the terminal part 114, and a sensor provided in the handpiece 200 may be connected to the control part 230 through wires provided inside the handpiece 200.

Embodiment 2

FIGS. 13 to 18 are schematic diagrams illustrating ultrasonic surgical devices according to various embodiments of the present invention, and in the following description, a redundant explanation will be omitted as to the same illustration and explanation of the ultrasonic surgical device in the above-described Embodiment 1.

The ultrasonic surgical device 2000 (or 2000-1 in FIG. 15) according to an embodiment of the present invention may include a cartridge 2100 and a handpiece 200. The cartridge 2100 may be attached to/detached from the handpiece 200. In another embodiment, a handpiece and a cartridge may be integrally implemented with a handpiece, rather than being attached to/detached from the handpiece. In an embodiment, the cartridge 2100 may include a cartridge housing 2110, an ultrasonic therapy part, a window 2115 and a driving part 2140.

Figure 15:
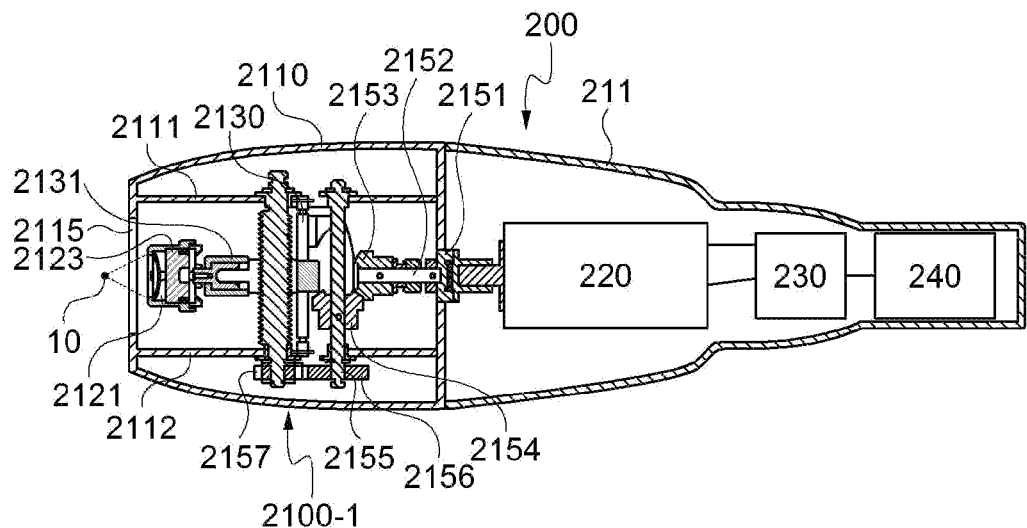
FIG. 15 is a schematic diagram illustrating a modified example of the ultrasonic surgical device according to another embodiment of the present invention.

In an embodiment, the cartridge housing 2110 may be a kind of a case defining the outer walls of the cartridge 2100 (or 2100-1 in FIG. 15).

In an embodiment, the ultrasonic therapy part may include a transducer 2121 provided inside the cartridge housing 2110 and generating IFU waves. In an embodiment, the IFU waves generated by the transducer 2121 may be transferred to an exterior of the cartridge 2100 via a window 2115.

In an embodiment, the driving part 2140 may perform a function of moving the ultrasonic therapy part, specifically, the transducer 2121. Here, the transducer 2121 may move forward or backward inside the cartridge housing 2110.

In an embodiment, while the transducer 2121 is moving forward, heights of the transducer 2121 may vary. For example, supposing that the IFU waves are downwardly emitted from the transducer 2121, the relative height of the transducer 2121 may increase or decrease inside the cartridge housing 2110. In addition, the transducer 2121 may move while passing at least one or more sections, including a first section (S1 of FIG. 18) in which the height of the transducer 2121 increases as the transducer 2121 moves forward, and a second section (S2 of FIG. 18) in which the height of the transducer 2121 decreases as the transducer 2121 moves forward.

Although not shown, as the transducer 2121 moves backward, the height of the transducer 2121 may also vary. In addition, sections in which the height of the transducer 2121 increases according to backward movement of the transducer 2121, and sections in which the height of the transducer 2121 decreases according to backward movement of the transducer 2121, may also be implemented.

In an embodiment, if the transducer 2121 ascends, the distance between the transducer 2121 and the window 2115 may increase. If the transducer 2121 descends, the distance between the transducer 2121 and the window 2115 may decrease. Here, the distance (D1 of FIG. 18) between the transducer 2121 and the window 2115 in a case where the transducer 2121 is positioned highest, is greater than the distance (D2 of FIG. 18) between the transducer 2121 and the window 2115 in a case where the transducer 2121 is positioned lowest.

Figure 16:
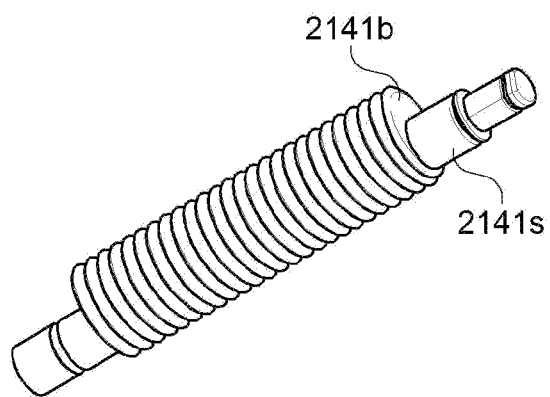
FIG. 16 is a schematic diagram illustrating a major part of the ultrasonic surgical device according to an embodiment of the present invention.
Figure 17:
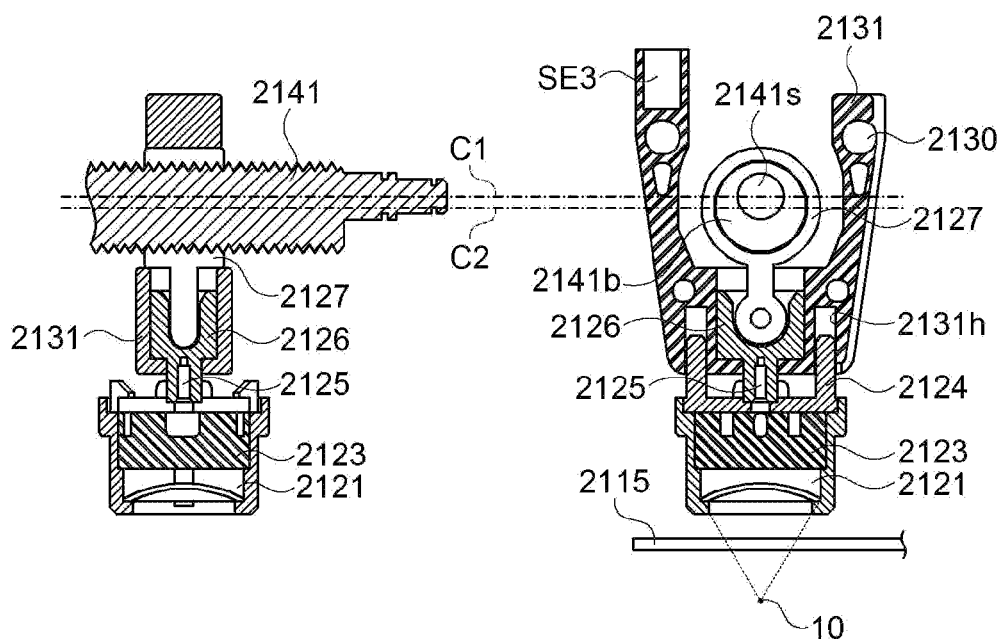
FIG. 17 is a schematic diagram illustrating a major part of the ultrasonic surgical device according to an embodiment of the present invention.

In an embodiment, the driving part 2140 may include an eccentric driving cam 2141. The eccentric driving cam 2141 may be installed to rotate about a predetermined rotation axis inside the cartridge housing 2110. In an embodiment, the eccentric driving cam 2141 may be shaped of a cylinder, and the rotation axis of the eccentric driving cam 2141 may be spaced apart from a cylindrical center axis. In an embodiment, as illustrated in FIGS. 16 and 17, the eccentric driving cam 2141 may include a body part 2141b and a shaft 2141s. Here, the rotation axis of the shaft 2141s may be called a shaft spine C1, and the center axis of the body part 2141b may be called a cam shaft C2. The shaft spine C1 and the cam shaft C2 may be spaced a predetermined distance apart from each other and may be parallel with each other.

In an embodiment, the rotation axis of an eccentric driving cam 2141 may be the same with the shaft spine C1. That is to say, as the shaft 2141s rotates about the shaft spine C1, the eccentric driving cam 2141 may also rotate about the shaft spine C1. In addition, according to the rotation of the eccentric driving cam 2141, the cam shaft C2 of the body part 2141b may also rotate about the shaft spine C1.

In an embodiment, the shaft 2141s and the body part 2141b may be integrally implemented with each other. In another embodiment, the shaft 2141s and the body part 2141b may be made of different materials. Particularly, the shaft 2141s may be implemented to be shaped of a pin using a material having a high strength, such as a metal, and the body part 2141b may be implemented using a synthetic resin having a relatively low strength and capable of easily implementing a predetermined shape or an unevenness. Accordingly, the manufacturing efficiency of the eccentric driving cam 2141 may be enhanced, while lowering a probability of causing a deformation to the eccentric driving cam 2141. Meanwhile, although not shown, various kinds of protrusions or grooves are formed on the shaft 2141s, which is incorporated in the eccentric driving cam 2141 as a frame in the course of molding the body part 2141b using a variety of molding processes, including extrusion, injection, compression, or casting, thereby rotatably coupling the shaft 2141s and the body part 2141b, which are made of different materials, to each other in an integrated manner.

Figure 13:
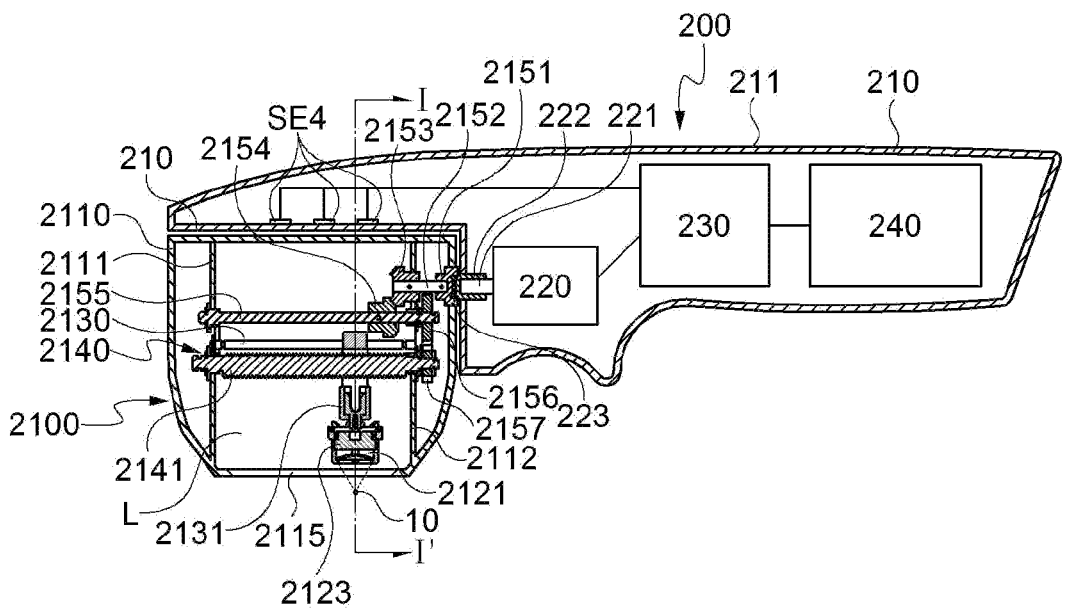
FIG. 13 is a schematic diagram illustrating an ultrasonic surgical device according to another embodiment of the present invention.
Figure 14:
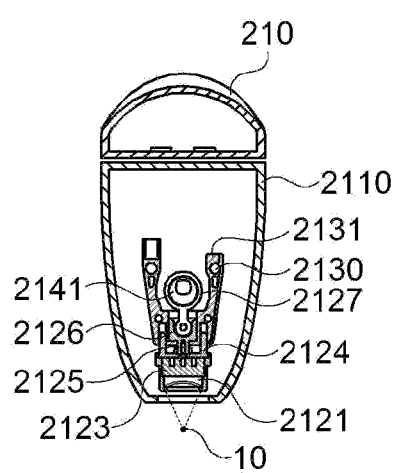
FIG. 14 is a schematic diagram illustrating an ultrasonic surgical device according to another embodiment of the present invention.

In an embodiment, means for fixing the eccentric driving cam 2141 may be provided inside the cartridge housing 2110. As illustrated in FIG. 13, a first frame 2111 is provided at the other side of the cartridge 2100 to allow the other end of the eccentric driving cam 2141 to be rotatably coupled thereto, and a second frame 2112 is provided at one side of the cartridge 2100 to allow the one end of the eccentric driving cam 2141 to be rotatably coupled thereto.

Meanwhile, a second rotating part 2151 having at least a portion exposed to the exterior of the cartridge housing 2110 may be physically directly or indirectly connected to the one end of the eccentric driving cam 2141, thereby rotating the eccentric driving cam 2141 according to rotation of the second rotating part 2151. The expression "an element being indirectly connected to another element" used herein may mean that a predetermined medium may be present between the two elements. In an embodiment, referring to FIG. 13, the cartridge housing 2110 may be physically connected to eccentric driving cam 2141 through a medium including a first gear shaft 2152, a first gear 2153, a second gear 2154, a second gear shaft 2155, a third gear 2156 and a fourth gear 2157. Accordingly, a rotation force (torque) derived from the rotation of the second rotating part 2151 may be transferred to the eccentric driving cam 2141. This connection mechanism may be similarly applied to an ultrasonic surgical device 2000-1 according to the embodiment illustrated in FIG. 15. Therefore, even if the rotation axis of a motor 220 and the rotation axis of the eccentric driving cam 2141 cross at right angle, a rotation force (torque) derived from the rotation of the second rotating part 2151 may be efficiently transferred to the eccentric driving cam 2141. However, one skilled in the art will readily understand that the number of gears or gear shafts or the arrangement thereof can be appropriately changed depending on the needs.

In an embodiment, in order to prevent the medium L filling the inner space of the cartridge housing 2110 from being effused, a sealing member (not shown) for securing air tightness may be further provided.

Successively, referring to FIG. 13, the motor 220 may be provided in the handpiece 200, and a first rotating part 222 connected to a motor drive shaft 221 may impart the rotation force (torque) to the second rotating part 2151. Here, an uneven part 223 may be provided on at least one of the first rotating part 222 and the second rotating part 2151 in a coupling region thereof, thereby reducing a loss in the rotation force while transferring the rotation force.

In an embodiment, as illustrated in FIG. 13, the rotation axis of the eccentric driving cam 2141 may be parallel with the motor drive shaft 221. In another embodiment, as illustrated in FIG. 15, the rotation axis of the eccentric driving cam 2141 may be perpendicular to the drive shaft of the motor 220.

In an embodiment, although not shown, a circuit board for connecting a power source or signal lines may be provided in the cartridge 2100. The cartridge 2100 and the handpiece 200 may be electrically connected to each other using the circuit board.

In an embodiment, the ultrasonic therapy part may be movably coupled to the eccentric driving cam 2141. In addition, as the eccentric driving cam 2141 rotates, the ultrasonic therapy part may ascend while moving forward, may descend while moving forward, may ascend while moving backward and may descend while moving backward.

In an embodiment, the ultrasonic therapy part may further include a connector 2126 and a connecting rod 2127 as well as a transducer 2121. Here, one side of the connecting rod 2127 is coupled to the eccentric driving cam 2141, and the other side of the connecting rod 2127 is connected to the connector 2126. The connector 2126 may be directly or indirectly connected to the transducer 2121.

In an embodiment, a screw thread or a screw groove may be formed on an outer surface of the eccentric driving cam 2141 to be brought into contact with one side of the connecting rod 2127. Here, as the eccentric driving cam 2141 rotates, the body part 2141b may rotate while repeatedly ascending and descending with respect to the shaft spine C1. When the body part 2141b ascends, the connecting rod 2127 may also ascend together with the body part 2141b, and when the body part 2141b descends, the connecting rod 2127 may also descend together with the body part 2141b.

In an embodiment, the connecting rod 2127 may be shaped of a ring, and body part 2141b may be coupled inside the ring. In an embodiment, at least a portion of the inner surface of the ring-shaped connecting rod 2127 and at least a portion of the outer surface of the eccentric driving cam 2141 may be screw-coupled to each other. Accordingly, as the eccentric driving cam 2141 rotates, the connecting rod 2127 may repeatedly ascend and descend while moving forward.

Meanwhile, the other side of the connecting rod 2127 may be coupled to the connector 2126, and the connector 2126 may be directly or indirectly connected to the transducer 2121. When the connector 2126 and the connector 2126 are indirectly connected to each other, they may be connected to each other by means of some elements.

In an embodiment, a transducer housing 2123 may be provided to connect the transducer 2121 to other elements while protecting the transducer 2121. In addition, one side and the other side of a connecting pin 2125 may be coupled to the transducer housing 2123 and the connector 2126, respectively.

Each of the ultrasonic surgical devices 2000 and 2000-1 may further include a guide arm 2131. In an embodiment, the guide arm 2131 may function to guide movement of the transducer 2121. In an embodiment, even if the body part 2141b repeatedly ascends and descends while moving forward, the movement of the transducer 2121 may be guided by the guide arm 2131, thereby constantly maintaining the orientation of ultrasonic waves irradiated from the transducer 2121. Accordingly, the safety and accuracy of the operation can be improved.

In an embodiment, the guide arm 2131 may move forward or backward in a state in which it is supported by the guide rail 2130. In an embodiment, the guide rail 2130 may be fixed inside the cartridge housing 2110 so as to be parallel with the rotation axis (shaft spine C1) of the eccentric driving cam 2141. For example, one end of the guide rail 2130 may be coupled to the first frame 2111, and the other end of the guide rail 2130 may be coupled to the second frame 2112. Meanwhile, a throughhole is provided in the guide arm 2131, and the guide rail 2130 may be coupled to the guide arm 2131 inside the throughhole to allow the guide rail 2130 to pass through the throughhole. In addition, the guide rail 2130 may be shaped of a straight line parallel with the eccentric driving cam 2141.

In an embodiment, the guide arm 2131 includes a space for accommodating the connector 2126. Here, as at least a portion of the outer surface of the connector 2126 is supported by the guide arm 2131, the connector 2126 may ascend or descend. To this end, the connector 2126 may have the outer surface shaped of a pillar, including, for example, a cylinder or a square pillar. A portion of the guide arm 2131, where the connector 2126 is to be accommodated, may be shaped to correspond to the connector 2126.

In an embodiment, the other side of the connecting rod 2127 may be rotatably coupled to the connector 2126. As the eccentric driving cam 2141 rotates, one side of the connecting rod 2127 may ascend and descend and may axially move on a surface perpendicular to the rotation axis of the eccentric driving cam 2141. For example, if the connecting rod 2127 is shaped of a ring covering the body part 2141b, the center of the ring may overlap with the cam shaft C2. A path established when the cam shaft C2 rotates according to the rotation of the eccentric driving cam 2141 rotates may be the same as that established by the center of the ring of the connecting rod 2127. Here, as the other side of the connecting rod 2127 is rotatably coupled to the connector 2126, the connector 2126 may be supported by the guide arm 2131 to then stably ascend and descend even if one side of the connecting rod 2127 is moved along a path similar to the cam shaft C2.

In an embodiment, one end of the connecting pin 2125 may be coupled to the transducer housing 2123, and the other end of the connecting pin 2125 may be coupled to the connector 2126. Here, a portion of the guide arm 2131 may be positioned between the transducer housing 2123 and the connector 2126. In this case, the connecting pin 2125 may pass through the guide arm 2131.

In an embodiment, a guide pin 2124 upwardly protruding from the transducer 2121 may further be provided. The guide pin 2124 may be coupled to the transducer 2121 by means of the transducer housing 2123. In addition, a guide pin hole 2131h shaped to correspond to the guide pin 2124 may be provided in the guide arm 2131. Here, the guide pin hole 2131h may support the guide pin 2124 while the guide pin 2124 ascends and descends, thereby allowing the transducer 2121 to repeatedly ascend and descend more stably while moving forward.

Figure 18:
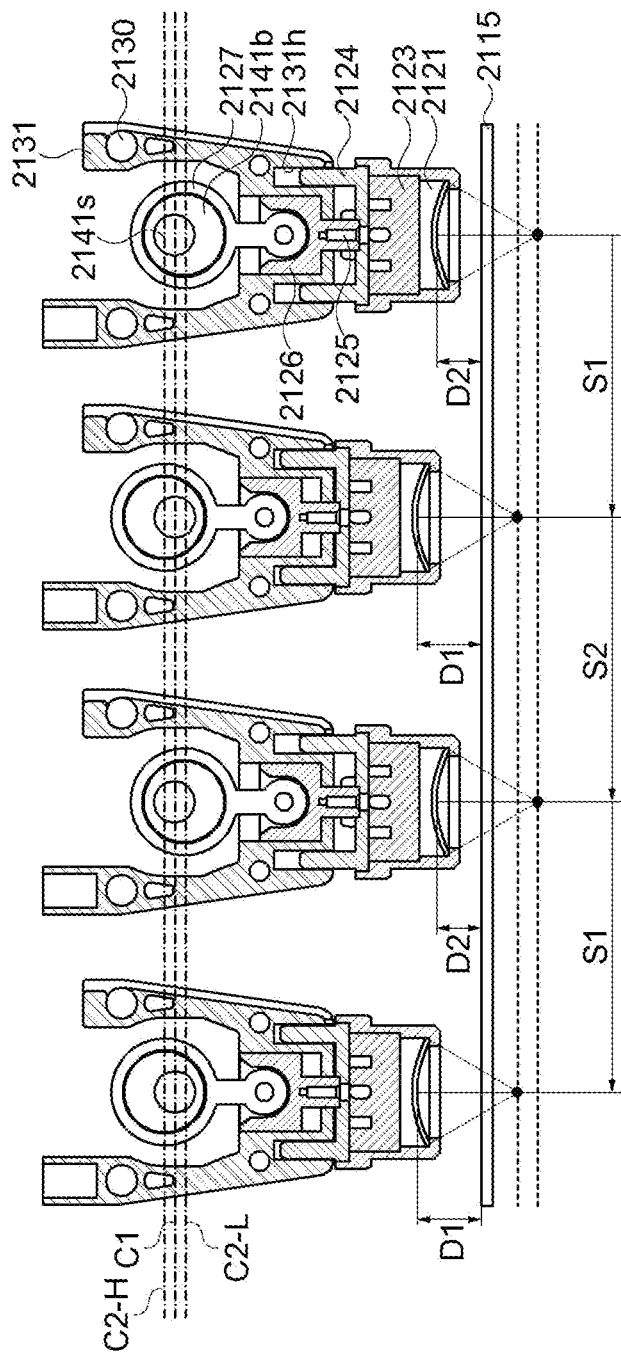
FIG. 18 is a diagram for explaining an operating principle of the ultrasonic surgical device according to an embodiment of the present invention.

Referring to FIG. 18, as the eccentric driving cam 2141 rotates, the transducer 2121 positioned at one side of the eccentric driving cam 2141 may ascend while moving forward, which is shown as a first section S1. In addition, as the eccentric driving cam 2141 rotates, the transducer 2121 may descend while moving forward, which is shown as a second section S2. Meanwhile, the shaft spine C1 may be a rotation center of the eccentric driving cam 2141, and is maintained at a constant height even with the rotation of the eccentric driving cam 2141. However, as the eccentric driving cam 2141 rotates, the cam shaft C2, which is the center axis of the body part 2141b, is repeatedly changed to be positioned at the lowest point C2-L and the highest point C2-H. Accordingly, the distance between the transducer 2121 and the window 2115 repeatedly increases and decreases in the range between the minimum value D2 and the maximum value D1.

According to an embodiment of the present invention, the position of the transducer 2121 can be detected. To this end, various kinds of sensors, including an IR sensor, a hall sensor, or a photo sensor, may be employed.

In an embodiment, as illustrated in FIG. 17, the guide arm 2131 may include a third sensor SE3. Here, the third sensor SE3 may be implemented by the IR sensor. If the third sensor SE3 includes an IR emitting part, an IR receiving part may be positioned opposite to the third sensor SE3 (e.g., a spot positioned on the first frame 2111).

In another embodiment, the third sensor SE3 may include an IR emitting part and an IR receiving part. In this case, a reflecting part (not shown) made of a material capable of reflecting IR rays may be positioned opposite to the first sensor SE1. In the structure illustrated in FIG. 13, the reflecting part may be provided in the first frame 2111.

In an embodiment, a fourth sensor SE4, which is implemented by at least one or more hall sensors or photo sensor, may be provided at an upper portion of the cartridge 2100. Here, the fourth sensor SE4 may be provided in the handpiece 200. In this case, the cartridge housing 2110, etc. needs to be implemented using a material that does not interrupt the fourth sensor SE4 in detecting the position of the ultrasonic therapy part 120. For example, if the fourth sensor SE4 is implemented by a photo sensor, components positioned between a reference region for detecting the position of the ultrasonic therapy part 120, and the fourth sensor SE4, including the cartridge housing 2110, are preferably made of a material having high transmissivity. Accordingly, the fourth sensor SE4 provided in the handpiece 200 may be shared by multiple cartridges 2100. In another embodiment, the fourth sensor SE4 may be provided within the cartridge housing 2110. In this case, however, the manufacturing cost of the cartridge 2100 may undesirably rise.

This work was supported by the Technological Innovation R&D Program (S2459280) funded by the Small and Medium Business Administration (SMBA, Korea). Project S2459280 entitled [Development of IFU-imaging convergence system for treatment of primary axillary hyperhidrosis]

INDUSTRIAL APPLICABILITY

Since the ultrasonic surgical device according to an embodiment of the present invention is used in a variety of operations, including an operation for alleviating hyperhidrosis, an operation for skin beauty care, an operation for obesity treatment, or the like, it can be applied to various fields of the beauty industry, the medical industry, and so on.

The invention claimed is:

1. An ultrasonic surgical device including a cartridge for irradiating ultrasonic waves, the cartridge comprising:
    a cartridge housing having an empty inner space filled with a medium;
    an ultrasonic therapy part which is movably provided inside the cartridge housing and includes a transducer for generating focused ultrasonic waves;
    a window through which the ultrasonic waves generated from the transducer pass; and
    a driving part which moves the ultrasonic therapy part inside the cartridge housing,
    wherein the driving part is shaped of a cylinder and includes an eccentric driving cam having a rotation axis spaced apart from a center axis of the cylinder; the ultrasonic therapy part includes a connecting rod having one side coupled to an outer surface of the eccentric driving cam and a connector coupled to the other side of the connecting rod; and
    wherein the transducer moves in one direction according to clockwise rotation of the eccentric driving cam, and as the transducer moves in the one direction, the distance between the window and the transducer repeatedly increases and decreases.

2. The ultrasonic surgical device of claim 1, wherein the one direction ranges from one end to the other end of the cartridge housing; wherein if the eccentric driving cam rotates in a clockwise direction, the transducer moves in the one direction, and wherein if the eccentric driving cam rotates in a counterclockwise, the transducer moves from the other end to the one end of the cartridge housing, and as the transducer moves from the other end to the one end of the cartridge housing the distance between the window and the transducer repeatedly increases and decreases.

3. The ultrasonic surgical device of claim 1, further comprising a guide arm functioning to guide the ultrasonic therapy part to move forward, to move backward, to move upward and to move downward, as the orientation of a bottom surface of the transducer is constantly maintained on the basis of the window, wherein the connecting rod is rotatably coupled to the connector, and the connector ascends and descends while being supported on a surface contacting the guide arm.

4. The ultrasonic surgical device of claim 1, further comprising a guide arm functioning to guide the ultrasonic therapy part to move forward, to move backward, to move upward and to move downward, as the orientation of a bottom surface of the transducer is constantly maintained on the basis of the window, wherein the ultrasonic surgical device further includes a guide pin protruding upwardly relative to the transducer; the guide arm further includes a guide pin hole for accommodating the guide pin; and as the guide pin is supported on an inner wall of the guide pin hole, the transducer ascends and descends to make the orientation of the bottom surface of the transducer constantly maintained on the basis of the window.

5. The ultrasonic surgical device of claim 1, further comprising a guide arm functioning to guide the ultrasonic therapy part to move forward, to move backward, to move upward and to move downward, as the orientation of a bottom surface of the transducer is constantly maintained on the basis of the window, wherein the connecting rod is rotatably coupled to the connector; the connector ascends and descends as it is supported on a surface contacting the guide arm; the ultrasonic surgical device further includes a guide pin protruding upwardly relative to the transducer; and the guide arm further includes a guide pin hole for accommodating the guide pin; and as the guide pin is supported on an inner wall of the guide pin hole, the transducer ascends and descends to make the orientation of the bottom surface of the transducer constantly maintained on the basis of the window.

6. The ultrasonic surgical device of claim 5, further comprising a guide rail disposed to be parallel with a rotation axis of the driving cam inside the cartridge housing, wherein the guide arm moves forward and backward while being supported on the guide rail.

7. The ultrasonic surgical device of claim 1, wherein the eccentric driving cam comprises:
   a shaft made of a metallic material; and
   a body part shaped of a cylinder and made of a synthetic resin, wherein the rotation axis of the eccentric driving cam is a center axis of the shaft.

8. The ultrasonic surgical device of claim 1, wherein one side of the connecting rod is shaped of a ring covering the eccentric driving cam.

9. The ultrasonic surgical device of claim 1, wherein the driving part comprises:
   a driving cam rotatably coupled inside the cartridge housing; and
   a first recess provided along the outer surface of the driving cam, and
   the ultrasonic therapy part comprises:
   a guide part fixed to the transducer; and
   an insertion pin having one side movably inserted into the first recess along the first recess and the other side fixed to the transducer or the guide part,
   wherein the trajectory of a first contact point having the shortest distance from the rotation axis of the driving cam, among contact points between the insertion pin and the first recess, is established according to the rotation of the driving cam, such that the distance between the rotation axis of the driving cam and the first contact point increases or decreases.

10. The ultrasonic surgical device of claim 9, further comprising an elastic member that generates an elastic force allowing the insertion pin to be pressed toward the first recess.

11. The ultrasonic surgical device of claim 9, further comprising a guide rail disposed to be parallel with the rotation axis of the driving cam inside the cartridge housing, wherein the guide part further includes a guide groove into which the guide rail is inserted, and a distance between a top surface of the guide rail and the guide groove increases or decreases.

12. The ultrasonic surgical device of claim 1, wherein the driving part comprises:
   a driving cam rotatably coupled inside the cartridge housing; and
   a first protrusion provided along the outer surface of the driving cam, and the ultrasonic therapy part comprises:
   a guide part fixed to the transducer,
   wherein one side of the first protrusion is brought into contact with the transducer or the guide part; and the trajectory of a second contact point having the shortest distance from the rotation axis of the driving cam, among contact points between the first protrusion and the transducer or the guide part, is established according to the rotation of the driving cam, such that the distance between the rotation axis of the driving cam and the second contact point increases or decreases in a spiral form.

13. The ultrasonic surgical device of claim 12, further comprising an elastic member that generates an elastic force allowing the transducer or the guide part to be pressed toward the first recess.

14. The ultrasonic surgical device of claim 9, wherein the one direction ranges from one end to the other end of the cartridge housing; and the transducer passes a first section in which the distance between the window and the transducer increases and a second section in which the distance between the window and the transducer decreases while moving in the one direction.

15. The ultrasonic surgical device of claim 1, further comprising a position sensor for detecting the position of the transducer.

* * * * *